United States Patent [19]

Haeussling et al.

[11] Patent Number: 5,736,068
[45] Date of Patent: Apr. 7, 1998

[54] TRIPHENYLENE COMPOUNDS AND PREPARATION OF DISCOTIC LIQUID CRYSTALLINE CROSSLINKED POLYMERS

[75] Inventors: Lukas Haeussling, Laubenheim; Dirk Funhoff, Heidelberg; Karl Siemensmeyer, Frankenthal; Karl-Heinz Etzbach, Frankenthal; Friedrich Closs, Frankenthal; Helmut Ringsdorf; Peter Schuhmacher, both of Mainz, all of Germany

[73] Assignee: BASF Aktiengesellschaft, Ludwigshafen, Germany

[21] Appl. No.: 649,693

[22] PCT Filed: Nov. 8, 1994

[86] PCT No.: PCT/EP94/03649

§ 371 Date: May 22, 1996

§ 102(e) Date: May 22, 1996

[87] PCT Pub. No.: WO95/14652

PCT Pub. Date: Jun. 1, 1995

[30] Foreign Application Priority Data

Nov. 23, 1993 [DE] Germany ............... 43 39 711.5

[51] Int. Cl.$^6$ ............... C09K 19/32; C09K 19/52; C09K 19/34; F21V 9/00
[52] U.S. Cl. ............... 252/299.62; 252/299.01; 252/299.61; 252/299.6; 252/582
[58] Field of Search ............... 252/299.62, 299.01, 252/299.67, 299.61, 299.6, 582

[56] References Cited

U.S. PATENT DOCUMENTS 4,333,709  6/1982  Dubois et al. ............... 359/103 X
4,430,650  2/1984  Billard ............... 340/784
4,631,143  12/1986  Praefcke et al. ............... 252/299.62
4,865,762  9/1989  Kreuder et al. ............... 252/299.01
4,980,081  12/1990  Ringsdorf et al. ............... 252/299.01
5,308,535  5/1994  Scheuble et al. ............... 252/299.01

FOREIGN PATENT DOCUMENTS 254 060   1/1988  European Pat. Off. .
385329    9/1990  European Pat. Off. .
504059    6/1992  European Pat. Off. .
3827046   3/1990  Germany .

OTHER PUBLICATIONS

Bechgaard et al., *J. Am. Chem. Soc.*, vol. 94, pp.
Piatelli et al., *Tetrahedron*, 1965, vol. 21, pp. 3229–3236.
Matheson et al., *Chem. Comm.*, no. 13, 1965, pp. 278–279.
van der Pol et al., *Macromolecules*, 1990, vol. 23, pp. 155–162.
Fox et al., *C&EN*, vol. 71, pp.38–48, 1993.
Kurihara et al., *Mol. Crystl. Ordered Fluids*, vol. 4, pp. 57–74, 1984.
LeBarny et al., *Liq. Crystl. Ordered Fluids*, vol. 4, pp. 57–74, 1984.
Chapuzet et al., *Tetrahedron*, vol. 47, no. 4/5, pp. 791–798, 1991.
Collard et al., *J. of Amer. Chem. Society*, vol. 113, no. 23, Nov. 6 1991.
Shenouda et al., *Polym. Prepr.*(Am. Chem. Soc., Div. Polym. Chem.), vol. 33, no. 1, pp. 1048–9, 1992.

*Primary Examiner*—Cynthia Harris Kelly
*Attorney, Agent, or Firm*—Keil & Weinkauf

[57] ABSTRACT

Novel triphenylene compounds which contain, bonded to the triphenylene framework, at least three ethylenically unsaturated groups or groups carrying oxiranyl or thiiranyl groups, and a process for the preparation of discotic liquid crystalline crosslinked polymers.

5 Claims, No Drawings

TRIPHENYLENE COMPOUNDS AND PREPARATION OF DISCOTIC LIQUID CRYSTALLINE CROSSLINKED POLYMERS

This application is a 371 of PCT/EP 94/03649 filed Nov. 8, 1994.

The present invention relates to novel triphenylene compounds, processes for the preparation of discotic liquid crystalline crosslinked polymers using these novel triphenylene compounds and the use of the crosslinked polymers as charge transport materials, for example in photocopiers or in laser printers.

Photoconductor coatings based on inorganic substances, for example on selenium, tellurium or cadmium, and those based on organic polymers are already known. Thus, the production of drum coatings of organic polymers by photochemical methods is described, for example, in EP-A-0 504 059.

Organic photoconductors (OPC) are mainly used as photosensitive materials in electrophotography and the printing industry.

Aspects of the interaction of light with discotic liquid crystalline systems are described in the publication by A. M. Fox et al. in C & EN 71 (1993), 38–48.

Van der Pol et al. (Macromolecules 23 (1990) 155) describe the synthesis and properties of discotic liquid crystalline metallophthalocyanines having the functionality of eight. It is true that thermal crosslinking gives insoluble liquid crystalline materials which have increased electrical conductivity, particularly after doping with iodine. However, utilization of the photoconductivity is technically impossible here since it is superposed by the high intrinsic conductivity.

The photoconductive properties of low molecular weight liquid crystals in the discotic phase or one of the kalamitic liquid crystalline phases (cf. for example EP-A 254 060) are also known. In the case of these, however, the mechanical stability in the liquid crystalline phase is not guaranteed. Furthermore, polymeric discotic liquid crystalline phases, possibly doped with trinitrofluorenone, are known and are proposed for use as photoconductors (cf. U.S. Pat. No. 4,865,762). However, such polymeric systems have serious disadvantages in the orientation, since it is not possible to achieve defect-free orientation of the columns in the discotic liquid crystalline phase.

In some of the coating processes currently employed, toxic substances are used and in some large amounts of organic solvents are released, which make it more difficult to comply with special regulations on reduction of emissions. Moreover, the organic photoconductors used at present have very low charge carrier mobilities.

Discotic liquid crystalline triphenylenes have excellent photoconductivity in the liquid crystalline phase, which is due to the molecular orientation of the substance. However, this technical advantage cannot be used in the conventional OPC technology since the liquid crystalline properties are lost.

It is an object of the present invention to provide novel polyfunctional compounds which are suitable for the preparation of discotic liquid crystalline crosslinked polymers, the prior art disadvantages described above being avoided.

We have found that this object is achieved and that, surprisingly, the applied layer can be crosslinked and cured by direct application of a polymerizable mixture of triphenylene compounds polysubstituted by polymerizable functions and subsequent thermal and/or photochemical polymerization. Particularly owing to the mild photochemical polymerization procedure, the special arrangement for increased conductivity is not destroyed.

The present invention relates to compounds of the general formula (I)

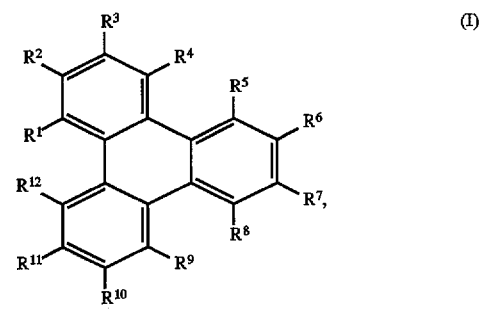

where $R^1$ to $R^{12}$ are identical or different and are each hydrogen, halogen, alkyl, X-alkyl, where X is O, S or NH, or N(alkyl)$_2$, where each alkyl radical is 1 to 20 carbon atoms, or are each such additionally substituted alkyl radicals or are each radicals which contain C—C double bonds, C—C triple bonds, oxiranyl groups or thiiranyl groups, with the proviso that at least three of the radicals $R^1$ to $R^{12}$ are radicals containing C—C double bonds, C—C triple bonds or oxiranyl or thiiranyl groups.

Particularly suitable radicals containing C—C double bonds are those of the general formulae

YZ—CH=CH$_2$,  YZ—C(CH$_3$)=CH$_2$,  Y—CO—CH=CH$_2$,

Y—CO—C(CH$_3$)=CH$_2$,  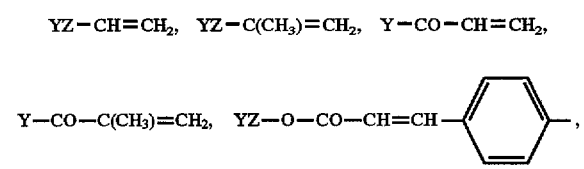

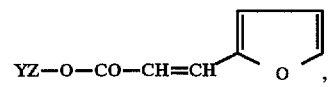

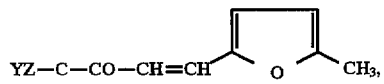

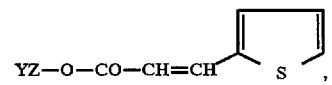

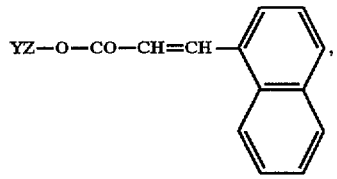

-continued

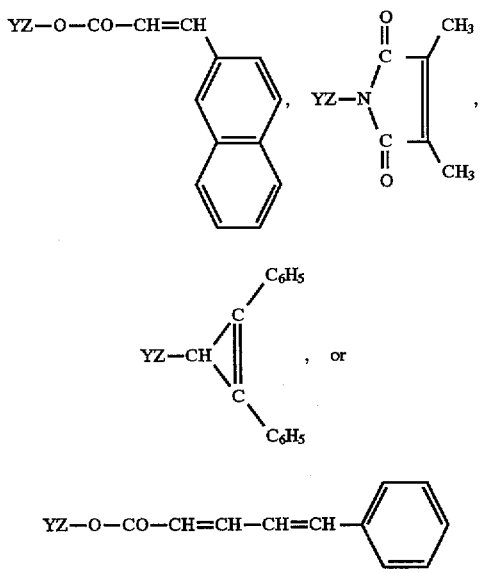

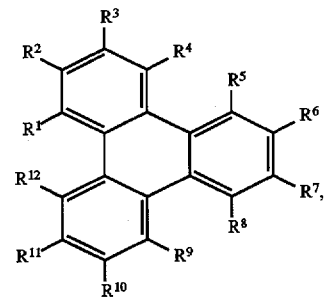

where Y is O, S or a single bond, Z is $(CH_2)_n$ and n is from 1 to 12.

If, in the formula (I), $R^1$ to $R^{12}$ are additionally substituted alkyl of 1 to 20 carbon atoms, they may contain, as substituents, COOH, OH, NCO, $NH_2$, $NHR^{13}$, $N(R^{13})_2$ or $OR^{13}$, where $R^{13}$ is straight-chain or branched alkyl of up to 12 carbon atoms, aryl, alkaryl, oxaalkyl having up to 4 oxygen atoms and up to 8 carbon atoms in the chain or thiaalkyl having up to 4 sulfur atoms in the chain.

Preferred novel compounds of the general formula (I) are those in which from three to six of the radicals $R^1$ to $R^{12}$ are radicals containing C—C double bonds, C—C triple bonds, or oxiranyl or thiiranyl groups.

The present invention furthermore relates to a process for the preparation of discotic liquid crystalline crosslinked polymers, said polymers being prepared by polymerization of compounds of the general formula (I), if necessary as a mixture with other copolymerizable ethylenically unsaturated compounds or compounds carrying oxiranyl or thiiranyl groups.

The present invention also relates to the use of the discotic liquid crystalline crosslinked polymers prepared by this process as charge transport materials, and the use of these charge transport materials in photocopiers or in laser printers.

Regarding the novel compounds, their preparation and their further processing and use, the following may be stated specifically.

In the novel compounds of the general formula (I)

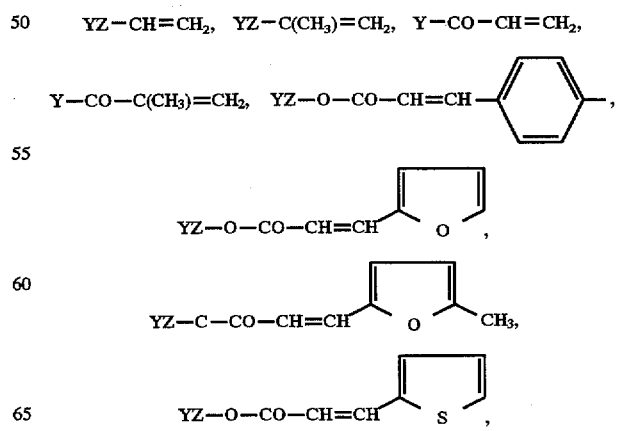

$R^1$ to $R^{12}$ may be identical or different and are each hydrogen, halogen, e.g. F, Cl or Br, alkyl of 1 to 20 carbon atoms, where the alkyl radicals may be straight-chain or branched or may contain alicyclic groups, for example methyl, ethyl, n-propyl, isopropyl, n-butyl, isobutyl, tert-butyl, hexyl, cyclohexyl, heptyl, octyl, 2-ethylhexyl, lauryl, palmityl or stearyl, X-alkyl where the alkyl radical is of 1 to 20 carbon atoms and X is O, S or NH, for example methoxy, ethoxy, propoxy, butoxy, pentyloxy, hexyloxy, heptyloxy, octyloxy, nonyloxy, decyloxy or undecyloxy, alkylthio, e.g. methylthio to undecylthio, NH-alkyl, e.g. methylamino to undecylamino, $N(alkyl)_2$, e.g. dimethylamino, diethylamino, methylethylamino, dipropylamino, dibutylamino or diundecylamino, additionally substituted alkyl of 1 to 20 carbon atoms which carries, as substituents, groups such as COOH, OH, NCO, $NH_2$, $NHR^{13}$, $N(R^{13})_2$, $OR^{13}$ or $COOR^{13}$, where $R^{13}$ is straight-chain or branched alkyl of up to 10 carbon atoms, e.g. methyl, ethyl, n-propyl, isopropyl, n-butyl, isobutyl, pentyl or hexyl, aryl, e.g. phenyl or biphenyl or terphenyl, alkaryl, e.g. benzyl or phenylethyl, oxaalkyl having 1 to 4 oxygen atoms and 1 to 8 carbon atoms, e.g. 1,3,6-trioxaoctane, thiaalkyl having 1 to 4 sulfur atoms and 1 to 8 carbon atoms in the chain, where at least three, preferably from three to six, of the radicals $R^1$ to $R^{12}$ are radicals containing C—C double bonds, C—C triple bonds or oxiranyl or thiiranyl groups.

Particular examples of radicals containing C—C double bonds are those of the abovementioned general formulae, i.e.

$YZ-CH=CH_2$, $YZ-C(CH_3)=CH_2$, $Y-CO-CH=CH_2$, $Y-CO-C(CH_3)=CH_2$, $YZ-O-CO-CH=CH-$⌬$-$,

-continued
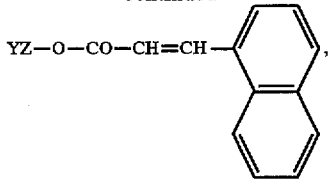
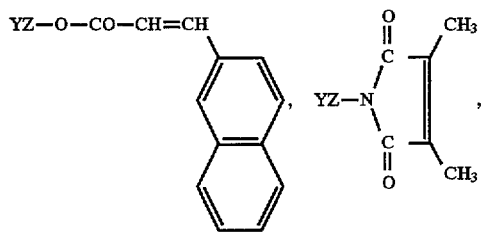
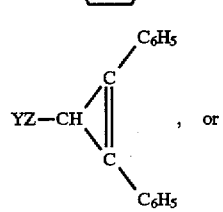
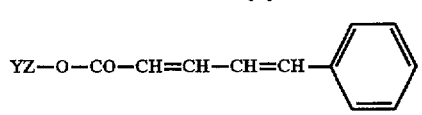
where Y is O, S or a single bond, Z is $(CH_2)_n$ and n is from 1 to 12.
Examples of such radicals $R^1$ to $R^{12}$ are $CH_2=CH-$, $CH_2=CH-O-$, $CH_2=CH-S-$, $CH_2=CH-CH_2-$, $CH_2=CH-CH_2-O-$, $CH_2=C(CH_3)-$, $CH_2=C(CH_3)-O-$, $CH_2=C(CH_3)-S-$, $CH_2=C(CH_3)-CH_2-$, $CH_2=C(CH_3)-CH_2-O-$, $CH_2=CH-CO-O$, $CH_2=C(CH_3)-CO-O$, $CH_2=C(CH_3)-CO-S-$,
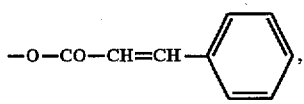
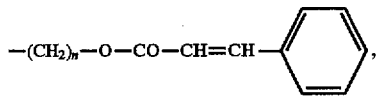
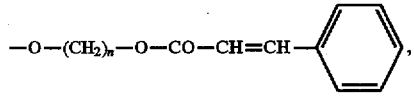
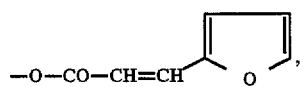
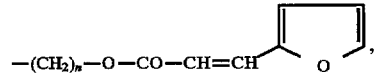
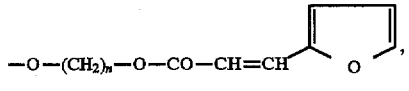
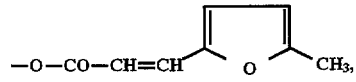
-continued
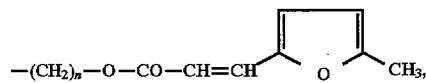
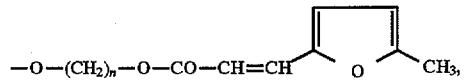
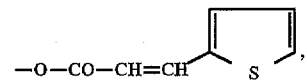
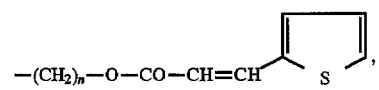
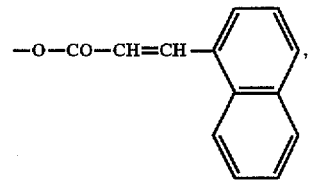
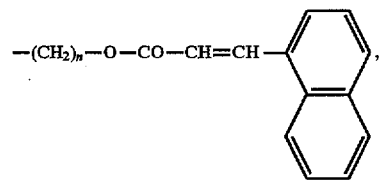
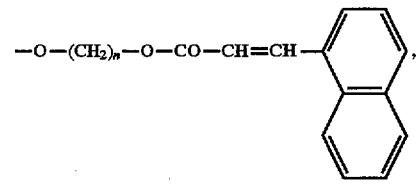
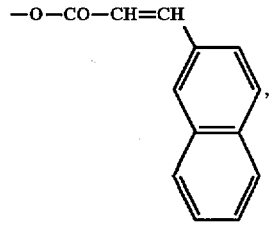
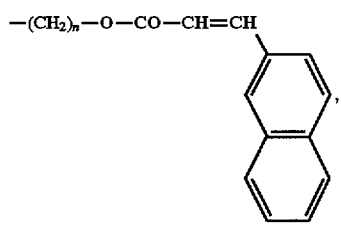

-continued

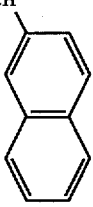

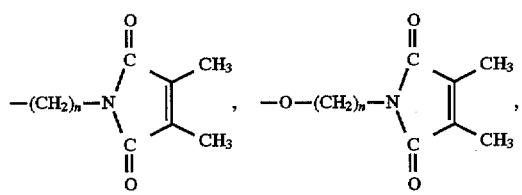

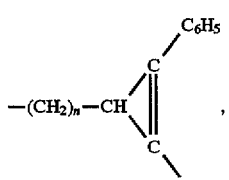

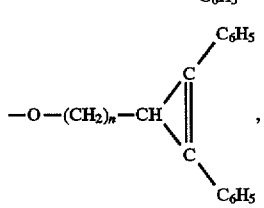

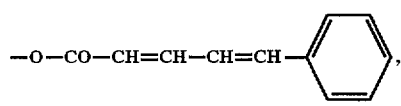

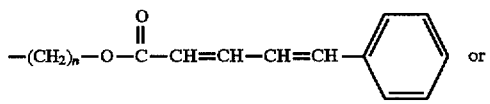 or

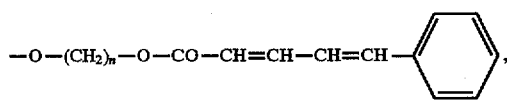

where in each case n is from 1 to 12, preferably from 3 to 6.

Particularly preferred radicals $R^1$ to $R^{12}$ containing C—C double bonds are 1-oxypropyl-3-acryloyl and 1-oxyhexyl-6-oxyvinyl.

Examples of radicals $R^1$ to $R^{12}$ containing C—C triple bonds are ethynyl and diacetylenyl.

Examples of radicals containing oxiranyl groups are

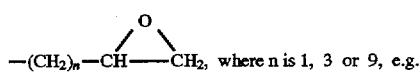

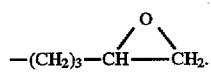

Examples of radicals containing thiiranyl groups are

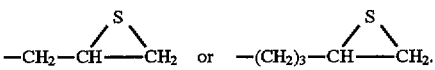

The novel compounds of the general formula (I) can be prepared by conventional processes, as described, for example, in I. M. Matheson, O. C. Musgrave and C. J. Webster, Oxidation of veratrole by quinones, Chem. Commun. 1965, 278, M. Piatelli, E. Fattorusso, R. A. Nicolaus and S. Magno, The structure of melanins and melanogenesis-V, Tetrahedron 21 (1965), 3229 and K. Bechgaard and V. D. Parker, Mono-, Di- and Trications of Hexamethoxytriphenylene, A Novel Anodic Trimerization, J. Am. Chem. Soc. 94 (1972), 4749.

Starting from the substitution pattern of 2,3,6,7,10,11-hexakis(pentyloxy)triphenylene, there are in principle two methods for introducing either one functional group for side group polymers or two or more functional groups for main chain polymers:

Either one or more of the six pentyl radicals can be eliminated from the hexapentyloxytriphenylene, leaving behind functional groups, or the pentyl radicals can be introduced via hexaacetoxytriphenylene so that unconverted acetoxy groups remain as reactive sites in the molecule.

The first synthesis step for functionalization by alkylation of the hexaacetoxytriphenylene is the synthesis of the aromatic system. The oxidative trimerization of veratrole, which can be carried out with p-chloranil or iron chloride or electrochemically, gives the triphenylene framework in the highest yield.

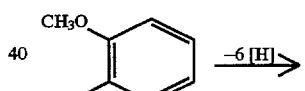

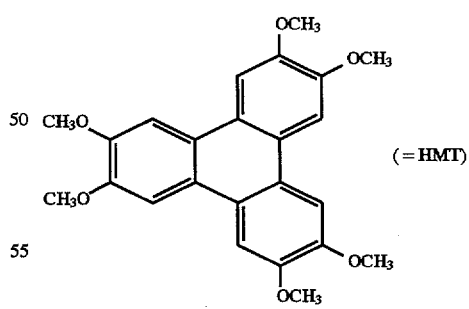

An advantageous modification of the oxidative trimerization by p-chloranil is the addition of silica gel as a carrier for the HMT, which is obtained as a fine, scarcely filterable foam in the heterogeneous reaction. This makes it possible to change rapidly from the aggressive reaction medium (1:1 sulfuric acid/acetic acid) to organic solvents during working up. The oxidation with iron chloride is also a synthesis route which may be used.

In the second step, the six methyl ether groups of the HMT may be replaced by base-labile acetyl protective groups. The ether cleavage may be effected with an excess of boron tribromide. The crystalline intermediate 2,3,6,7,10,11-triphenylenehexayl tris(o-bromoborate) can be transesterified in situ with acetic anhydride to give 2,3,6,7,10,11-triphenylenehexayl hexaacetate.

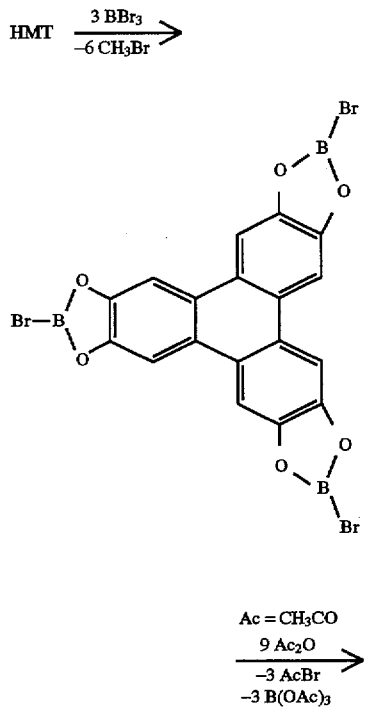

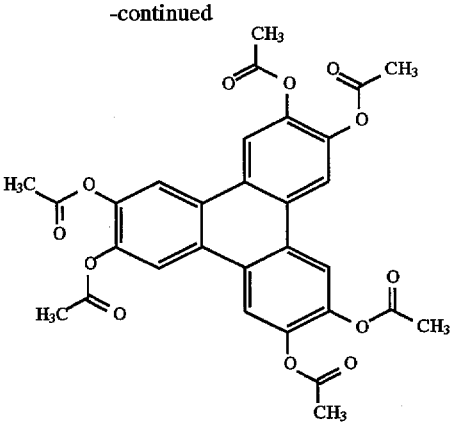

The hydroxyl- and/or alkoxy-containing triphenylenes which are suitable for the preparation of the novel compounds of the general formula (I) can be obtained, for example, by complete or partial ether cleavage of 2,3,6,7,10,11-hexaalkoxytriphenylene or by hydrolysis of the 2,3,6,7,10,11-triphenylenehexayl hexaacetate.

The hydroxyl- and/or alkoxy-containing triphenylenes can in turn be converted into novel compounds (I), for example by reaction with haloalkyl(meth)acrylates. Alternatively, novel compounds (I) may also be obtained by reacting hydroxyalkoxy-substituted triphenylenes with alkenoyl chlorides (for example (meth)acryloyl chloride). The product mixtures obtained in the reactions can be separated in a conventional manner by fractional crystallization or chromatography. Furthermore, randomly substituted triphenylenes can be prepared by simultaneous alkylation of the 2,3,6,7,10,11-hexahydroxytriphenylene with haloalkyl (meth)acrylates and alkyl halides.

Hexaalkoxytriphenylenes having alkyl chains of different lengths in the same molecule can be separated by chromatography.

Preferred compounds of the general formula (I) are those compounds in which at least three of the radicals $R^1$ to $R^{12}$ have C—C double bonds, in particular those having (meth) acryloyl groups, for example,

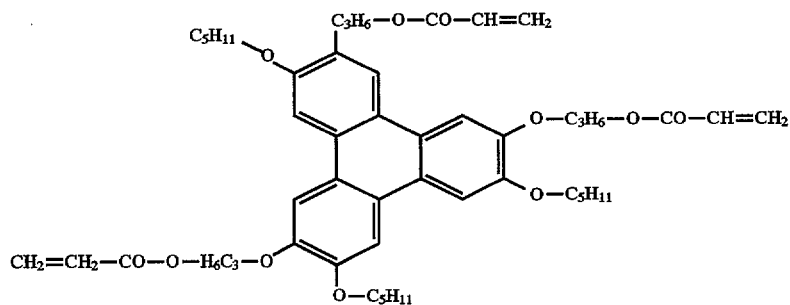

The preparation of discotic liquid crystalline crosslinked homo- or copolymers using the novel compounds of the general formula (I) may be carried out by the conventional polymerization processes, for example thermally in the presence of free radical polymerization initiators, e.g. azobisisobutyronitrile or benzoyl peroxide, preferably by photopolymerization at slightly below the clear point of the monomer or of the monomer mixture in the presence of suitable conventional photoinitiators, for example benzoin ethers, such as benzoin isopropyl ether, benzil dimethyl ketal or dimethylbenzoin ether, or acylphosphine oxide compounds, which may be used, for example, in amounts of from 0.1 to 10% by weight, based on the compounds of the formula (I).

It may be advantageous to copolymerize the novel compounds having the functionality of at least three, of the general formula (I), with bifunctional or in particular monofunctional compounds of the triphenylene type, for example together with pentakis-pentyloxyacryloylpropoxytriphenylene, and the amount of novel triphenylene compounds having the functionality of at least three should be from 20 to 80% by weight of the total amount of the monomer mixture.

For the preparation of the novel discotic liquid crystalline crosslinked polymers and their further use as charge transport materials in photocopiers or laser printers, it is advantageous to carry out the polymerization of the monomer or of the monomer mixture on certain substrates, for example on aluminum, steel or gold.

The novel discotic liquid crystalline crosslinked polymers can be prepared in a simple and environment-friendly manner since toxic compounds and waste gas emission are avoided.

The charge carriers prepared according to the invention are simple to produce, transport charge rapidly, are free of traps and do not form space charges.

EXAMPLE 1

Synthesis of Hexakis(vinyloxyethyloxy)-triphenylene

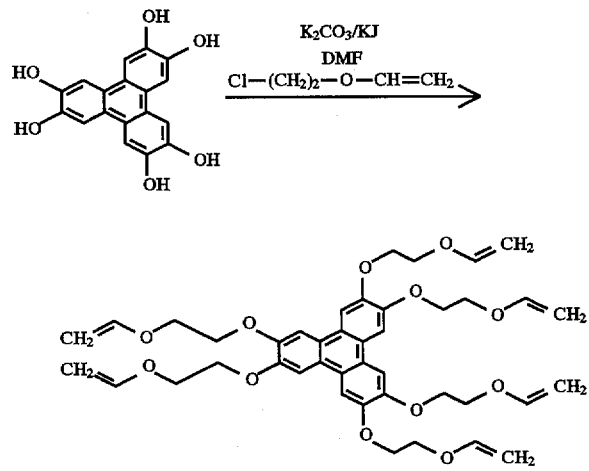

25.9 g of hexahydroxytriphenylene and 53.7 g of 2-chloroethyl vinyl ether were reacted with 41.8 g of potassium carbonate in a Claisen etherification. The solvent used was dimethylformamide (492.5 g). The batch was refluxed for 20 hours and then filtered over silica gel. The dimethylformamide was stripped off, and 5 g of the crude product were then purified by column chromatography (mobile phase: 1:1 dichloromethane/ethyl acetate).

Yield: 1.6 g

Melting behavior: k 108° C., $D_h$ 181° C. i

H-NMR(CDCl$_3$):

CH-aromat. 7.88 ppm

O—C$\underline{H}_2$— 6.65 ppm

—O—C$\underline{H}_2$— 4.4 ppm

—O—CH=CH$_2$— 4.2 ppm and 4.0 ppm

—O—CH$_2$—C$\underline{H}_2$—O— 3.89 ppm

EXAMPLE 2

Synthesis of Randomly Substituted Tris(2'-acryloyloxyethoxy)-tris(hexyloxy)-triphenylene a) Preparation of 2,3,6,7,10,11-hexahydroxytriphenylene 50.9 g of hexamethoxytriphenylene, 387 g of glacial acetic acid and 387 g of 47% strength aqueous hydrobromic acid were refluxed for 24 hours under nitrogen. The glacial acetic acid and the hydrobromic acid were then distilled off for the most part. The resulting dark blue-black substance was washed with three times 500 ml of water and dried under reduced pressure. The yield was 39.9 g.

b) Preparation of Randomly Substituted Tri-2'-acryloyloxy Ethoxy Trihexyloxytriphenylene 4.86 g (0,015 mol) of 2,3,6,7,10,11-hexahydroxytriphenylene were dissolved or suspended together with 8.66 g (0.0525 mol) of 1-bromohexane, 9.4 g (0.0525 mol) of 2-bromoethyl acrylate, 14.49 g (0.105 mol) of potassium carbonate and 0.1 g of phenothiazine in 50 ml of dimethylformamide and stirred for 6 hours at 80° C. under nitrogen. After cooling to room temperature, the mixture was precipitated in dilute hydrochloric acid, the product was extracted with methyl butyl ether and the ether phase was washed with water, dried with sodium sulfate and then evaporated down under reduced pressure. The crude product obtained was purified by column chromatography over silica gel (mobile phase: 1:1 toluene/ethanol) and then recrystallized from ethanol. 1.8 g of colorless crystals were obtained.

Melting point: 83°–87° C. The analysis by $^1$H-NMR indicated an average substitution of the triphenylene nucleus by 2.88 hexahexyloxy side chains and 3.12 2'-acryloyl ethoxy side chains.

EXAMPLE 3

Synthesis of Randomly Substituted Tris(4'-acryloyloxybutoxy)-tris(hexyloxy)-triphenylene a) Preparation of Randomly Substituted Tris(4'-acetyloyloxybutoxy)-tris(hexyloxy)-triphenylene [sic]

4.86 g (0.045 mol) of 2,3,6,7,10,11-hexahydroxytriphenylene were dissolved or suspended together with 10.24 g (0.05255 mol) of 4-bromobutyl acetate, 8.66 g (0.0525 mol) of 1-bromohexane and 14.49 g (0.105 mol) of potassium carbonate in 50 ml of dimethylformamide and stirred for 6 hours at 80° C. under nitrogen.

After cooling to room temperature, the mixture was precipitated in dilute hydrochloric acid, the product was extracted with methyl butyl ether and the ether phase was washed with water, dried with sodium sulfate and then evaporated down under reduced pressure. The crude product obtained was purified by column chromatography over silica gel (mobile phase: 1:1 toluene/ethanol). 10.9 g of colorless crystals were obtained.

The analysis of $^1$H-NMR indicated an average substitution of the triphenylene nucleus by 2.58 hexoxy side chains and 3.42 4'-acetyloyloxybutoxy [sic] side chains.

b) Preparation of Randomly Substituted Tris(4'-hydroxybutoxy)-tris(hexyloxy)-triphenylene 3.02 g of 50% strength aqueous potassium hydroxide solution and 40 ml of ethanol were added to 4.13 g (0.0045 mol) of tris(4'-acryloyloxybutoxy)-tris(hexyloxy)-triphenylene [sic] and the mixture was refluxed for 10 hours. After cooling to room temperature, the mixture was poured onto ice water, the precipitated product was extracted with methyl butyl ether and the ether phase was washed with water, dried with sodium sulfate and then evaporated down under reduced pressure. The crude product obtained was purified by column chromatography over silica gel (mobile phase: 4:1 toluene/ethanol). 2.2 g of colorless crystals were obtained.

The analysis by $^1$H-NMR indicated an average substitution of the triphenylene nucleus by 3 hexoxy side chains and 3 4'-hydroxybutoxy side chains.

c) Preparation of Randomly Substituted Tri-4'-acryloylbutoxytrihexyloxytriphenylene 6.7 g (0.093 mol) of acrylic acid, 0.1 g of 2,6-di-tert-butyl-p-cresol, 0.2 g of p-toluenesulfonic acid and 50 ml of 1,1,2-trichloroethane were added to 1.85 g (0.0023 mol) of tri-4'-hydroxybutoxytrihexyloxytriphenylene and the mixture was boiled for 24 hours under a water separator while stirring. After cooling to room temperature, the mixture was extracted with water and sodium bicarbonate solution, and the organic phase was dried with sodium sulfate and then evaporated down under reduced pressure. The crude product obtained was purified by column chromatography over silica gel (mobile phase: 1:1 toluene/ethanol). Ethanol was added to the product, the ethanol phase was digested at −30° C. 1.35 g of a colorless oil were obtained. The analysis by $^1$H-NMR indicated an average substitution of triphenylene nucleus by 3 hexoxy side chains and 3 4'-acryloyloxybutoxy side chains.

EXAMPLE 4

Preparation of 2,6,10-tris(3'-acryloyloxypropoxy)-3,7,11-tris(pentoxy)-triphenylene (I) and 2,6,11-tris(3'-acryloyloxypropoxy)-3,7,10-tris(pentoxy)-triphenylene (II) (Variant 1)

a) 2,6,10-trihydroxy-3,7,11-tris(pentoxy)-triphenylene and 2,6,11-trihydroxy-3,7,10-tris(pentoxy)-triphenylene Starting from 2,3,6,7,10,11-hexakis(pentoxy)-triphenylene, which could be prepared by alkylation of 2,3,6,7,10,11-hexahydroxy- or 2,3,6,7,10,11-hexaacetoxytriphenylene by a known method, the two isomers 2,6,10-trihydroxy-3,7,11-tris(pentoxy)-triphenylene and 2,6,11-trihydroxy-3,7,10-tris(pentoxy)-triphenylene were prepared by triple ether cleavage with 9-bromo-9-borobicyclo[3.3.1]nonane in methylene chloride.

For this purpose, 3.0 g of 2,3,6,7,10,11-hexapentyloxytriphenylene were dissolved in 30 ml of dichloromethane in a three-neck flask flushed with argon, and 18.1 ml of a 1 molar solution of 9-bromo-9-borobicyclo[3.3.1]nonene in methylene chloride were slowly added dropwise. The reaction mixture was then stirred for 30 hours at room temperature before 1.1 ml of ethanolamine were carefully added. After a few minutes, further dichloromethane and water were added and the product was extracted by shaking. The product-containing dichloromethane phase was dried with magnesium sulfate and the dichloromethane was distilled off. The two isomers were purified and separated by column chromatography using the mobile phase 3:2 dichloromethane/hexane and pure dichloromethane. Altogether, two white powders were obtained in a yield of 1.82 g (80.7% of theory). The yield of symmetric product 2,6,10-trihydroxy-3,7,11-tris(pentoxy)-triphenylene was 0.81 g (35.9%) and the yield of asymmetric product 2,6,11-trihydroxy-3,7,10-tris(pentoxy)-triphenylene was 1.01 g (44.8%). The two isomers were characterized by NMR and IR spectroscopy.

2,6,10-trihydroxy-3,7,11-tris(pentoxy)-triphenylene: $k_1$ 120.5° C. $k_2$ 140° C. i 2,6,11-trihydroxy-3,7,10-tris(pentoxy)-triphenylene: k 146° C. i b) 2,6,10-Tris(3'-hydroxypropoxy)-3,7,11-tris(pentoxy)-triphenylene and 2,6,11-tris(3'-hydroxypropoxy)3,7,10-tris(pentoxy)-triphenylene 700 mg (1.31 mmol) of 2,6,11-trihydroxy-3,7,10-tris(pentoxy)-triphenylene and 0.819 g (5.89 mmol) of bromopropanol were dissolved in 10 ml of 2-pentanone. After the addition of 5.5 g of potassiumn carbonate and 40 mg of potassium iodide, the mixture was heated for 6 hours at 80° C. (oil bath temperature). Thereafter, the reaction mixture was filtered to separate off the insoluble inorganic components and was washed with acetone. Distilling off the solvent and subsequently carrying out chromatography over silica gel using 11:1.2 [sic] dichloromethane/ethyl acetate as the mobile phase gave 412 mg (44.4% of theory) of a white product.

$R_f$(CH$_2$Cl$_2$/MeOH: 10/1)=0.50; phase behavior: k 86 296 D$_h$ 110 i:

Elemental analysis: C$_{42}$H$_{60}$O$_9$ (M$_w$=708.93): Calc. C: 71.16%, H: 8.53%, found C: 70.46%, H: 8.43%, $^1$H-NMR (200 MHz, CDCl$_3$): δ (ppm)=8.0–7.73 (m, 6H, H$_{arom.}$), 4.41 (t, 6H, OC$\underline{H}_2$CH$_2$CH$_2$OH, J=5.7 Hz), 4.23–4.15 (m, 6H, OC$\underline{H}_2$(CH$_2$)$_3$CH$_3$), 3.96 (t, 6H, OCH$_2$CH$_2$C$\underline{H}_2$OH, J=4.9 Hz), 2.95 (s, 3H, O$\underline{H}$), 2.23–2.15 (m, 6H, OCH$_2$C$\underline{H}_2$CH$_2$OH), 2.00–1.87 (m, 6H, OCH$_2$C$\underline{H}_2$(CH$_2$)$_2$CH$_3$), 1.58–1.34 (m, 12H, OCH$_2$C$\underline{H}_2$(CH$_2$)$_2$CH$_3$), 0.95 (t, 15H, C$\underline{H}_3$, J=6.9 Hz);

FD-MS: m/z: 7098.4 [M]$^+$.

Furthermore, the symmetrically substituted 2,6,10-trihydroxy-3,7,11-tris(pentoxy)-triphenylene were obtained in a yield of 40% similarly to this method.

c) 2,6,10-Tris(3'-acryloyloxypropoxy)-3,7,11-tris(pentoxy)-triphenylene and 2,6,11-tris(3'-acryloyloxypropoxy)-3,7,10-tris(pentoxy)-triphenylene 500 mg (0.71 mmol) of 2,6,11-trihydroxy-3,7,10-tris(pentoxy)-triphenylene, 1.5 ml of triethylamine and a pinch of 2,6-di-tert-butyl- p-cresol were dissolved in 5 ml of dichloromethane. 210 mg (2.33 mmol) of acryloyl chloride (dissolved in 3 ml of dichloromethane) were then added dropwise while cooling with ice and under an argon atmosphere. The mixture was slowly warmed up to room temperature and stirred for a further 20 hours. It was then diluted with 20 ml of dichloromethane and extracted with 1 normal sodium bicarbonate solution and water. After the solvent had been stripped off, a chromatographic purification was effected over silica gel using 60:1 dichloromethane/methanol as the mobile phase, and the product was then recrystallized from ethanol. The yield of white 2,6,11-tris(3'-acryloyloxypropoxy)-3,7,10-tris(pentoxy)-triphenylene was 129.4 mg (21.1% of theory).

$R_f$ ($CH_2Cl_2$/MeOH 300:1)=0.34; m.p.: 68° C.;

Elemental analysis: $C_{51}H_{66}O_{12}$ ($M_w$=871.08); Calc. C: 70.32%, H: 7.64%, found C: 69.92%, H: 7.23%;

$^1$H-NMR (200 MHz, $CDCl_3$); δ (ppm)=7.84+7.81 (2×s, 6H, $H_{arom}$), 6.41 (dd, 3H, COCH=$CH_2$) $J_{trans}$=17.3 Hz, $J_{gem}$=1.5 Hz), 6.13 (dd, 3H, COC$H$=$CH_2$, $J_{cis}$=10.3 hZ, $J_{trans}$=17.2 hZ), 5.81 (dd, 3H, COCH=$CH_2$, $J_{cis}$=10.3, $J_{gem}$=1.5 Hz), 4.47 (t, 6H, OC$H_2$($CH_2$)$_2$OCO, J=6.3 Hz), 4.32 (t, 6H, O($CH_2$)$_2$$CH_2$OCO, J=6.1 Hz), 4.21 (t, 6H, OC$H_2$($CH_2$)$_3$$CH_3$, J=6.6 Hz), 2.36–2.23 (m, 6H, OCH$_2$C$H_2$$CH_2$O), 2.00–1.86 (m, 6H, OCH$_2$C$H_2$($CH_2$)$_2$$CH_3$), 1.61–1.34 (m, 12H, OCH$_2$CH$_2$(C$H_2$)$_2$$CH_3$), 0.95 (t, 9H, $CH_2$C$H_3$, J=6.9 Hz);

FD-MS: m/z: 870.5 [M].$^+$

Furthermore, the symmetrically substituted 2,6,10-tris(3'-acryloyloxypropoxy)-3,7,11-tris(pentoxy)-triphenylene was obtained in a yield of 26% similarly to this method.

EXAMPLE 5

2,6,10-tris(3'-acryloyloxypropoxy)-3,7,11-tris(pentoxy)-triphenylene and 2,6,11-tris(3'-acryloyloxypropoxy)-3,7,10-tris(pentoxy)-triphenylene (Variant 2)

a) 1-Hydroxy-2-pentoxybenzene 95.1 g (0.69 mol) of potassium carbonate and 321.2 g of methyl isobutyl ketone were added to 137.64 g (1.25 mol) of pyrocatechol and 188.63 g (1.25 mol) of 1-bromopentane, and the mixture was then refluxed for 23 hours. The mixture was cooled, after which the potassium carbonate was filtered off and the methyl isobutyl ketone was distilled off under reduced pressure. The oily residue was then subjected to fractional distillation over a short column under reduced pressure from an oil pump. 127.3 g of 1-hydroxy-2-pentoxybenzene were obtained at 5 bar and a boiling point of 88°–92° C.

b) 1-(3'-Hydroxypropoxy)-2-pentoxybenzene 50.1 g (0.36 mol) of potassiumn carbonate and 115.6 g of methyl isobutyl ketone were added to 124 g (0.69 mol) of 1-hydroxy-2-pentoxybenzene and 100.8 g (0.69 mol), after which the mixture was refluxed for 40 hours. The mixture was cooled, after which the potassium carbonate was filtered off and the methyl isobutyl ketone was distilled off under reduced pressure. The oily residue was then subjected to fractional distillation over a short column under reduced pressure from an oil pump. 78.2 g of 1-(3'-hydroxypropoxy)-2-pentoxybenzene were obtained at 5 mbar and a boiling point of 140°–148° C.

c) 2,6,10-Tris(3'-hydroxypropoxy)-3,7,11-tris(pentoxy)-triphenylene and 2,6,11-Tris(3'-hydroxypropoxy)-3,7,10-tris(pentoxy)-triphenylene 1 g (4.2 mmol) of 1-(3'-hydroxypropoxy)-2-pentoxybenzene was dissolved in 5 ml of dichloromethane under an argon atmosphere. 1.59 g (9.8 mmol) of iron(III) chloride were added a little at a time, after which 3 drops of concentrated sulfuric acid were introduced and the mixture was heated to an oil bath temperature of 50° C. After 2 hours, the reaction mixture was cooled and terminated by adding 5 ml of methanol. The solvent was distilled off and the product was purified by chromatographing twice. The mobile phase was 30:1 dichloromethane/methanol the first time and 40:1 dichloromethane/methanol the second time. It was possible to separate the symmetric 2,6,10-tris(3'-hydroxypropoxy)-3,7,11-tris(pentoxy)-triphenylene completely from the asymmetric 2,6,11-tris(3'-hydroxypropoxy)-3,7,10-tris(pentoxy)-triphenylene. The yield was 543 mg for the asymmetric product and 80 mg for the symmetric product.

The subsequent esterification with acrylic acid was carried out similarly to Example 4.

EXAMPLE 6

A mixture of pentakis(pentoxy)-(acryloylpropoxy)-triphenylene (monofunctional, liquid crystalline) and tris(pentoxy)-tris(acryloyloxypropoxy)-triphenylene (trifunctional, not liquid crystalline) in a ratio of 4:1 was melted. The mixture had discotic liquid crystalline properties. After the addition of a free radical photoinitiator (1 mol % of benzil dimethyl ketal, e.g. Darocur® 1664 from CIBA-GEIGY AG), the mixture was polymerized with crosslinking by exposure to UV light from a medium pressure or high pressure mercury lamp at a temperature slightly below the clear point of the monomer mixture, i.e. in the liquid crystalline phase. Since the orientation of the molecules in the sample is not disturbed by the photopolymerization, photoconduction was observed both before and after the polymerization. This orientation was not destroyed even after heating up above the clear point of the liquid crystalline crosslinked copolymer and subsequent cooling. In addition, the copolymer had excellent surface characteristics and very good mechanical properties.

COMPARATIVE EXAMPLE

A mixture of 99 mol % of pentakis(pentoxy)-(acryloyloxypropoxy)-triphenylene (monofunctional, liquid crystalline) and 1 mol % of a photoinitiator (e.g. benzil dimethyl ketal, such as Darocur® 1664) in isotropene was melted at 98° C. The mixture exhibited discotic liquid crystalline behavior. The oriented phase prepared by cooling from the isotropene was polymerized by exposure to UV light.

When this polymerization batch was cooled to room temperature, it separated into polymeric and crystalline low molecular weight parts which, owing to their insufficient orientation, no longer conducted the photocurrent.

We claim:
1. A compound of the formula (I)

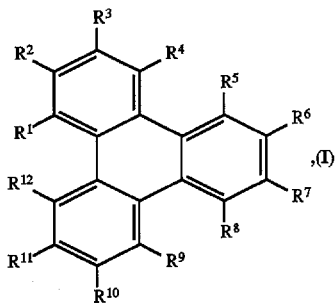

where $R^1$ to $R^{12}$ are identical or different and are each hydrogen, halogen, alkyl, X-alkyl, where X is O, S or NH, or N(alkyl)$_2$, where each alkyl radical is of 1 to 20 carbon atoms, or are each such additionally substituted alkyl radicals containing as substituents, COOH, OH, NCO, NH$_2$, NHR$^{13}$, N(R$^{13}$)$_2$, or OR$^{13}$, wherein R$^{13}$ is a straight chain or branched alkyl, of up to 12 carbon atoms, aryl, alkaryl, oxaalkyl having up to four oxygen atoms in the chain or thiaalkyl having up to 4 sulfur atoms in the chain, or are each radicals which contain C—C double bonds, C—C triple bonds, oxiranyl groups or thiiranyl groups, with the proviso that at least three of the radicals $R^1$ to $R^{12}$ are radicals containing oxiranyl or thiiranyl groups or radicals containing C—C double bonds, of the formulae

Y—CO—CH=CH$_2$, Y—CO—C(CH$_3$)=CH$_2$,

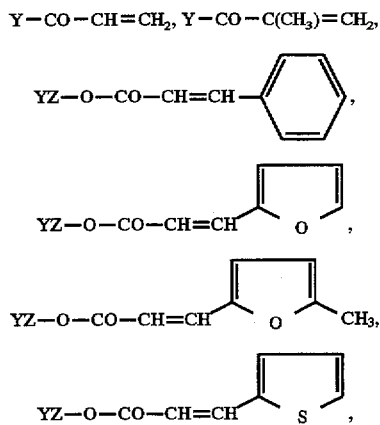

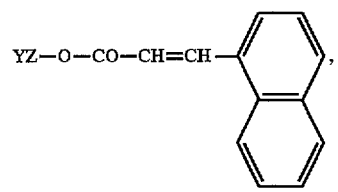

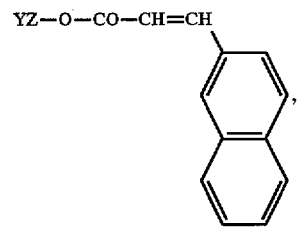

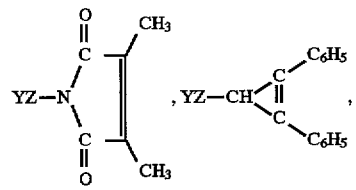

or 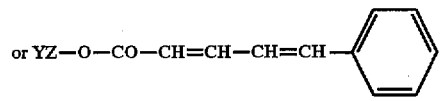

where Y is O, S or a single bond, Z is (CH$_2$)$_n$ and n is from 1 to 12.

2. A compound of the formula (I) as defined in claim 1, wherein from three to six of the radicals $R^1$ to $R^{12}$ are radicals containing C—C double bonds, C—C triple bonds or oxiranyl or thiiranyl groups.

3. A compound of the formula I as defined in claim 1, where $R^1$, $R^4$, $R^5$, $R^8$, $R^9$ and $R^{12}$ are hydrogen, three of $R^2$, $R^3$, $R^6$, $R^7$, $R^{10}$ and $R^{11}$ are hexyloxy, and three of $R^2$, $R^3$, $R^6$, $R^7$, $R^{10}$ and $R^{11}$ are acryloylethoxy.

4. A compound of the formula I as defined in claim 1, where X is O, NH or N(alkyl)$_2$.

5. A compound of the formula I as defined in claim 1, where X is O.

* * * * *

UNITED STATES PATENT AND TRADEMARK OFFICE
CERTIFICATE OF CORRECTION

PATENT NO.: 5,736,068

DATED: April 7, 1998

INVENTOR(S): HAEUSSLING et al.

It is certified that error appears in the above-identified patent and that said Letters Patent is hereby corrected as shown below:

Title page, item [30], "Nov. 23, 1993" should be --Nov. 22, 1993--.

Signed and Sealed this

Ninth Day of June, 1998

Attest:

BRUCE LEHMAN

Attesting Officer

Commissioner of Patents and Trademarks